United States Patent [19]

Sato et al.

[11] Patent Number: 4,613,571

[45] Date of Patent: Sep. 23, 1986

[54] POLYPRENYL SULFONE DERIVATIVES AND PROCESS FOR PRODUCING THE SAME

[75] Inventors: Akio Sato, Yatabemachi; Kenji Nakajima, Sakuramura; Yoshimasa Takahara, Narashino; Shizumasa Kijima, Niiza; Hideaki Watanabe, Kisogawamachi; Tamio Kawamura, Kakamigahara; Yasushi Nagai, Tokyo, all of Japan

[73] Assignees: Esai Co., Ltd.; General Director of the Agency of Industrial Science and Technology, both of Tokyo, Japan

[21] Appl. No.: 581,763

[22] Filed: Feb. 21, 1984

Related U.S. Application Data

[62] Division of Ser. No. 368,475, Apr. 14, 1982.

[30] Foreign Application Priority Data

Apr. 17, 1981 [JP]  Japan ............................ 56-58223

[51] Int. Cl.$^4$ .......................... F27B 9/02; F27D 5/00
[52] U.S. Cl. .................................. 435/130; 435/131; 435/253; 435/872
[58] Field of Search ............... 435/67, 130, 131, 136, 435/157, 253, 872; 568/28

[56]  References Cited

U.S. PATENT DOCUMENTS

| | | | |
|---|---|---|---|
| 3,304,323 | 2/1967 | Fonken et al. | 435/872 |
| 4,449,002 | 5/1984 | Sato et al. | 568/28 |
| 4,468,458 | 8/1984 | Sato et al. | 435/134 |
| 4,468,459 | 8/1984 | Sato et al. | 435/136 |
| 4,474,881 | 10/1984 | Sato et al. | 435/136 |

FOREIGN PATENT DOCUMENTS

| | | | |
|---|---|---|---|
| 0119087 | 9/1979 | Japan | 435/157 |
| 6099793 | 8/1981 | Japan | 435/157 |
| 0050892 | 3/1982 | Japan | 435/136 |
| 0150392 | 9/1982 | Japan | 435/157 |

Primary Examiner—Charles F. Warren
Assistant Examiner—R. Thomas Gallegos
Attorney, Agent, or Firm—Flynn, Thiel, Boutell & Tanis

[57]  ABSTRACT

There are disclosed polyprenyl sulfone derivatives of the general formula:

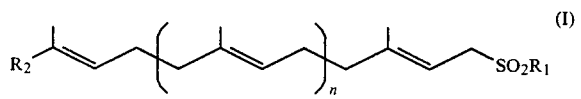

(I)

wherein n represents an integer of 1-4, $R_1$ represents an aryl group and $R_2$ represents a hydroxymethyl or carboxyl group. The polyprenyl sulfone derivatives are prepared by cultivating a microorganism of the genus Nocardia capable of oxidizing a compound of the general formula:

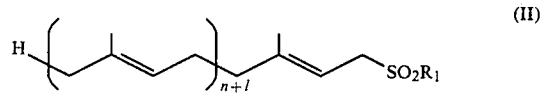

(II)

wherein n and $R_1$ have the same meanings as defined above, in a culture medium containing a compound of the above general formula (II), and then collecting the oxidation product from the culture mixture. The polyprenyl sulfone derivatives are useful as intermediates for preparing various useful polyprenyl compounds.

1 Claim, No Drawings

POLYPRENYL SULFONE DERIVATIVES AND PROCESS FOR PRODUCING THE SAME

This is a division of application Ser. No. 368,475, filed Apr. 14, 1982.

The present invention relates to polyprenyl sulfone derivative of the general formula:

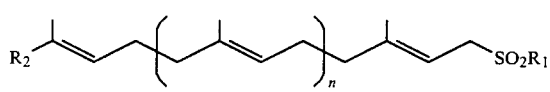
(I)

wherein n represents an integer of 1–4, $R_1$ represents an aryl group and $R_2$ represents a hydroxymethyl or carboxyl group, and a process for producing the same.

As the aryl group $R_1$ in the above general formula I, there can be mentioned, for example, phenyl, tolyl, xylyl, naphthyl or p-chlorophenyl groups.

It is known that polyprenyl compounds, such as polyprenyl alcohols and esters thereof, polyprenylcarboxylic acids and esters thereof and polyprenyl ketones, have anti-ulcer and hypotensive activities, as described in the specifications of Japanese Patent Laid-Open Nos. 144614/1977, 145922/1978, 5043/1979, 67037/1979 and 76513/1979. Further, it is known that polyprenyl alcohol is used as a starting material for preparing drugs, such as coenzyme $Q_{10}$. The compounds of the present invention are useful as intermediates in the syntheses of the above-mentioned and other useful polyprenyl compounds.

The final polyprenyl compounds can be synthesized from the compounds of the present invention by the carbon chain-elongation reaction disclosed in the specifications of, for example, Japanese Patent Laid-Open Nos. 103444/1978 and 103445/1978. When $R_2$ in the compound of the present invention is a hydroxymethyl group, the compound can be used, as such, as the intermediate. When $R_2$ is a carboxyl group, the compound is used after reducing the carboxyl group to a hydroxymethyl group. For example, a long-chain polyprenyl alcohol can be synthesized by the following process:

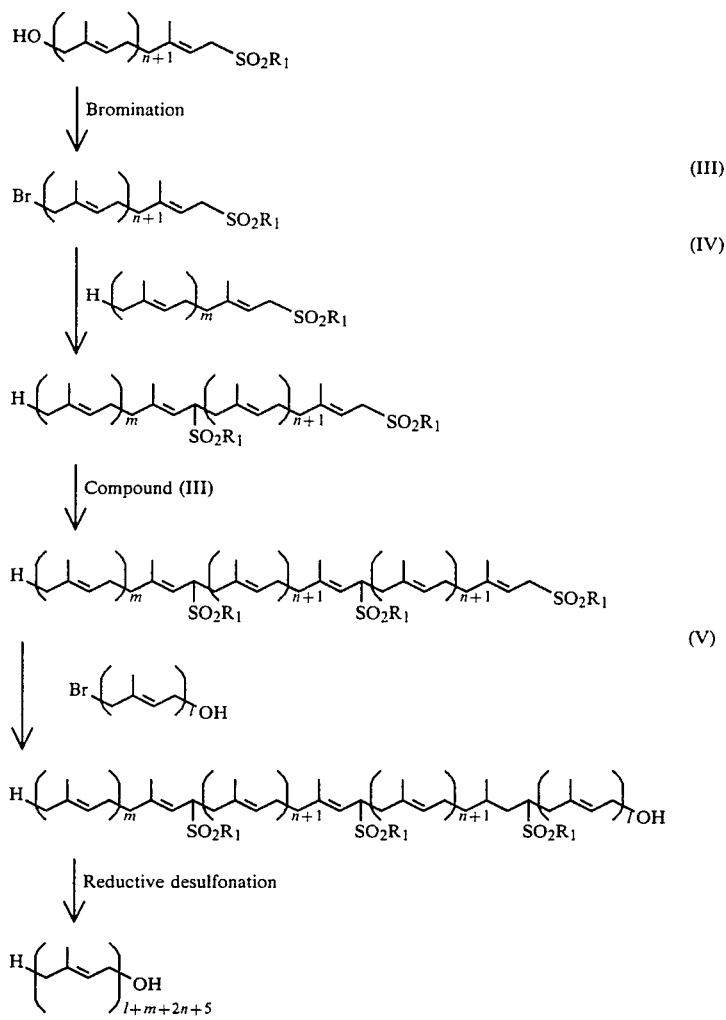

wherein n and $R_1$ have the same meanings as defined above and l an m each represent an integer.

The compound of general formula (III) is reacted twice in the above process. If the compound of formula (III) is reached additional times, a polyprenyl alcohol having a longer chain is obtained.

If a compound of the general formula:

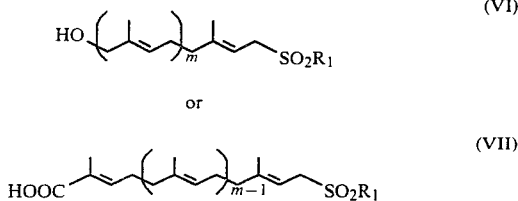

or

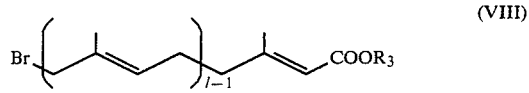

is used in the above reaction scheme in place of the compound of general formula (IV), a compound having a hydroxyl or carboxyl group at the other (leftward) end of the molecule is synthesized.

If a compound of the general formula:

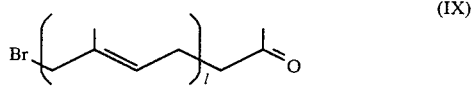

wherein $R_3$ represents a carboxylic acid-protective group or (IX)

is used in the above reaction scheme in place of the compound of general formula (V), a polyprenylcarboxylic acid derivative or polyprenyl ketone is synthesized.

As described above in detail, various polyprenyl compounds having a desired carbon chain length can be synthesized by using the compounds of the present invention as the intermediates.

As a compound related to the compounds of the present invention, 8-(p-tolylsulfonyl)-2,6-dimethyl-2,6-octadien-1-ol is disclosed in the specification of Japanese Patent Laid-Open No. 103445/1978. However, if this compound, which has a short carbon chain comprising two isoprene units, is used for the synthesis of a long-chain isoprenoid, according to the above-mentioned carbon chain elongation reaction, the reaction must be repeated several times. Therefore, it is advantageous to use a compound having a longer carbon chain like those of the present invention.

The above-mentioned 8-(p-tolylsulfonyl)-2,6-dimethyl-2,6-octadien-1-ol is obtained by oxidizing geranyl p-tolyl sulfone with selenium dioxide and then reducing the reaction product. There is known a process wherein an isoprenoid having a functional group at one end is reacted with selenium dioxide to oxidize the other end of the molecule. However, the yield is low in this oxidation process. Particularly, as the isoprene chain is elongated, as in the compounds of the present invention, the yield is lowered. In addition, the separation of an organic selenium compound, which is the by-product in this oxidation reaction, from the intended product is quite difficult even by column chromatography or distillation. Further, the above-mentioned oxidation process is not preferred as a process for synthesizing starting materials for preparing drugs, because the organic selenium compound is harmful to the human body.

After investigations of processes wherein microorganisms are used, the inventors have discovered that the compounds of formula (I) of the present invention can be produced by oxidation of a compound of the formula

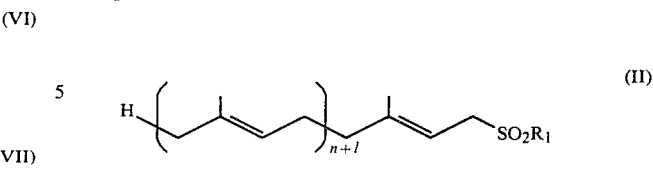

wherein n and $R_1$ have the same meanings as defined above, with a microorganism of the genus Nocardia. According to this process, the compounds of the present invention can be mass-produced by enlarging the scale of the culture process. The unreacted starting compound can be recovered easily and used again as the starting material. The process is thus highly efficient.

The BPM 1613 strain of genus Nocardia is effective for the production of the compounds of the present invention. Deposit of the BPM 1613 strain of genus Nocardia was made at the following depositary institutions, on the following dates and under the following accession numbers: (1) on Jan. 9, 1981 at the Institute for Fermentation, the address of which is 17–85, Juso-honmachi 2-chrome, Yodogawa-ku, Osaka, Japan, under accession number IFO 14101, and (2) on Sept. 18, 1972 at the Fermentation Research Institute, Agency of Industrial Science and Technology, the address of which is 1–3, Higashi 1-chrome, Yatabe-machi, Tsukuba-gun, Ibaraki-ken 305, Japan, under accession number FERM-P 1609. The BPM 1613 strain of genus Nocardia has the following microbiological properties. The color was determined according to "Color Standards" published by Nihon Shikisai Kenkyu-sho (Color Laboratory of Japan).

A. Form of cells:

This strain exhibits characteristic orange or pink color upon culture on almost all culture media as shown in the following culture properties. Young vegetative cells grow in a mycelial form, and branching is rarely observed. In an aged culture, the mycelium is divided to form bacillus ($0.4$–$0.6 \times 1.8$–$2.4\mu$). Gram staining: positive. The cells have no flagellum. The cells are not stained according to Ziehl-Nielsen's acid-fast staining method. Aerial mycelium is not observed.

B. Properties of BPM 1613 strain on various culture media:

(1) Sucrose-nitrate agar medium (30° C.): Poor growth; Color of colony: pink; No diffusing pigment.
(2) Glucose-asparagine agar medium (30° C.): No growth.
(3) Glycerol-asparagine agar medium (30° C.): Poor growth; Color of colony: pink; No diffusing pigment.
(4) Starch agar medium (30° C.): No growth.
(5) Tyrosine agar medium (30° C.): Poor growth; Color of colony: grayish white; No diffusing pigment.
(6) Nutrient agar medium (30° C.): Moderate growth; Color of colony: orange; No diffusing pigment.
(7) Yeast-malt agar medium (30° C.): Rich growth; Color of colony: orange; No diffusing pigment.
(8) Oatmeal agar medium (30° C.): Moderate growth; Color of colony: orange; No diffusing pigment.
(9) Calcium malate agar medium (27° C.): Moderate growth; Color of colony: pink.
(10) Egg-albumin medium (slant, 27° C.): Poor growth; Color of colony: white.
(11) Potato section medium (27° C.): Moderate growth; Color of colony: pale orange.

(12) Carrot section medium (27° C.): Moderate growth; Color of colony: pale pink.

C. Physiological properties:
(1) Growth temperature range (nutrient agar slant): 20°-42° C.
(2) Gelatin liquefaction: negative.
(3) Starch hydrolysis: negative.
(4) Skim milk coagulation and peptonization: negative.
(5) Litmus milk: no change.
(6) Melanine-like pigment formation: negative.
(7) Nitrate reduction: positive.
(8) Acid or gas formation from L-arabinose, D-xylose, D-glucose, D-fructose, sucrose, D-mannitol, glycerol, lactose, D-galactose, D-mannose, maltose, trehalose or starch: none.
(9) Catalase test: negative.
(10) Indole formation: negative.
(11) Hydrogen sulfide formation: negative.

D. Assimilation of carbon sources (on Pridham-Gottlieb agar medium, 30° C., 7 days):
L-arabinoze (+), D-xylose (+), D-glucose (++), D-fructose (++), sucrose (++), inositol (+), L-rhamnose (−), raffinose (+), D-mannitol (+).
++: moderate growth, +: poor growth, −: no growth.

The microorganism of this strain was cultured on Glycerol-Kelner-Morton medium according to a method of Arai et al. [Journal of General Applied Microbiology, 9, 119 (1963): The Actinomycetales, The Jena International Symposium on Taxonomy, 273 (1968)] and the infrared absorption spectrum thereof revealed that absorption bands characteristic to Nocardia (I: C & E types, II: C type, III: C type, IV: D type) were observed.

From the above properties, it was concluded that the microorganism under discussion belongs to the genus Nocardia, according to Bergey's Manual of Determinative Bacteriology, Seventh edition and Waksman's The Actinomycetes, Vol. 2.

The process for producing the compounds of the present invention will be described in detail.

A microorganism of the genus Nocardia capable of forming a compound of formula (I) by oxidizing a compound of the general formula:

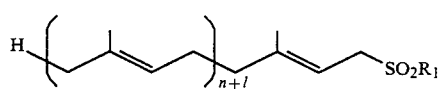
(II)

wherein n represents an integer of 1-4 and $R_1$ represents an aryl group, is cultured on a culture medium containing the compound of formula (II) and then the oxidation product is collected from the culture mixture whereby to obtain a compound of the present invention having the general formula:

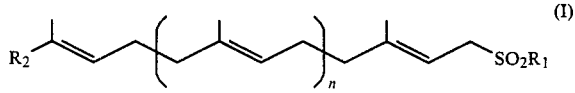
(I)

wherein n and $R_1$ have the same meanings as defined above and $R_2$ represents a hydroxymethyl or carboxyl group.

As the microorganism used in the process of the present invention, there can be employed any of those capable of oxidizing the compounds of formula (II) to form the compound of formula (I). As an example of them, there can be mentioned the BPM 1613 strain of genus Nocardia described above.

The culture process will be described below. As the carbon source, the compound of formula (II) is used. In addition, the culture medium can contain other conventional carbon sources. As the nitrogen source, there can be used, for example, a nitrate such as potassium, sodium or ammonium nitrate; an ammonium salt such as ammonium chloride, ammonium sulfate or ammonium phosphate; ammonia or urea. If necessary, an inorganic salt, such as potassium phosphate, sodium phosphate, magnesium sulfate, ferrous sulfate or manganese sulfate and an organic nutrient source, such as vitamins, amino acids, or yeast extract, corn steep liquor or malt extract containing vitamins and amino acids can be added to the culture medium. The pH of the medium is generally in the range of 6-8. The cultivation can be effected at 20°-40° C., under aerobic conditions for 2-5 days by, for example, the aerated shaking culture technique.

After completion of the cultivation, the compound of the present invention (formula (I)) can be separated from the culture mixture by extraction with an organic solvent. As the extraction solvent, there can be used, for example, diethyl ether, benzene, chloroform or ethyl acetate. The compound of the present invention can be isolated and purified by silica gel column chromatography.

The unreacted starting material can be recovered during the above extraction or column chromatography and used again as the starting material in a subsequent cultivation process.

A product having a hydroxymethyl or carboxyl group as the terminal group [$R_2$ in formula (I)] is obtained depending on the degree of oxidation caused by the microorganism. The composition of the product can be varied by varying the medium, culture time and the type of microorganism.

The following example will further illustrate the present invention.

EXAMPLE 1

Reaction Scheme:

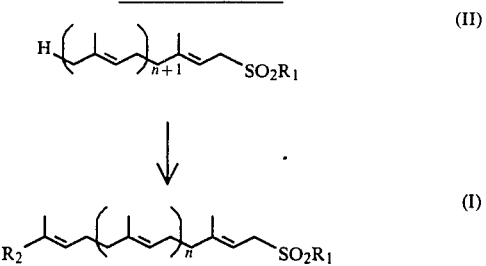

The strain (BPM 1613, FERM-P No. 1609) belonging to the genus Nocardia was precultivated under shaking at 30° C. for 4 days in a medium of 50 ml comprising 2% of n-paraffin, 0.5% of NaNO$_3$, 0.15% of KH$_2$PO$_4$, 0.15% of Na$_2$HPO$_4$, 0.05% of MgSO$_4$.7H$_2$O, 0.001% of FeSO$_4$.7H$_2$O, 0.001% of CaCl$_2$.2H$_2$O, and 0.02% of yeast extract and having the pH value of 7.2.

Then, the so obtained precultural broth was inoculated, in the volume ratio of 8 mm per 100 ml into a jar fermentor (for fermentation of 1 liter medium) containing a medium having the same composition as defined above except for substituting the n-paraffin (2%) by the compound of the general formula (II) (1%). The cultivation was carried out under the aeration-agitation conditions at 34° C. for 3 days. After completion of the cultivation, the mixture was subjected to extraction with ethyl acetate. Then the solvent was distilled off from the ethyl acetate extract. The residue was purified by silica gel column chromatography to isolate the main products. Hexane and diethyl ether were used as an eluting solvent.

The compounds obtained in various experiments, using different compounds of formula (II) as starting materials, are shown in the following Table 1.

Almost all of the unreacted starting compounds of general formula (II), were separately recovered as such, by the above silica gel column chromatography.

$$R_2\diagup\!\!\diagdown\!\diagup\!\!\diagdown\!\left(\!\diagup\!\!\diagdown\!\diagup\!\!\diagdown\!\right)_{\!n}\!\diagup\!\!\diagdown\!\diagup\!\!\diagdown\!SO_2R_1 \qquad (I)$$

wherein n is an integer of 1 to 4, $R_1$ is aryl and $R_2$ is hydroxymethyl or carboxyl, which comprises culturing the BPM1613 strain of the genus Nocardia capable of forming a compound of formula (I) by oxidizing a compound of the formula:

(II)

TABLE I

| n | $R_1$ | $R_2$ | Properties Yield (%) | Mass (M+) | NMR (δ, CDCl₃) |
|---|-------|-------|----------------------|-----------|-----------------|
| 1 | p-Tolyl | —COOH | Waxy 3.9 | 390 | 9.7 (1H, br), 7.75 (2H, d, J = 8Hz), 7.30 (2H, d, J = 8Hz), 6.88 (1H, t, J = 7Hz), 5.11 (1H, t, J = 8Hz), 5.02 (1H, t, J = 6Hz), 3.80 (2H, d, J = 8Hz), 2.44 (3H, s), 2.40–1.90 (8H), 1.84 (3H, s), 1.60 (3H, s), 1.35 (3H, s) |
|   |         | —CH₂OH | Oily 3.4 | 376 | 7.72 (2H, d, J = 8Hz), 7.30 (2H, d, J = 8Hz), 5.39 (1H, t, J = 6Hz), 5.18 (1H, t, J = 7Hz), 5.11 (1H, d, J = 6Hz), 3.90 (2H, s), 3.80 (2H, d, J = 8Hz), 2.44 (3H, s), 2.36–1.72 (9H), 1.67 (3H, s), 1.60 (3H, s), 1.35 (3H, s) |
| 2 | p-Tolyl | —COOH | Waxy 8.7 | 458 | 9.7 (1H, br), 7.75 (2H, d, J = 8Hz), 7.30 (2H, d, J = 8Hz), 6.88 (1H, t, J = 7Hz), 5.18 (1H, t, J = 7Hz), 5.11 (2H, br), 3.80 (2H, d, J = 8Hz), 2.44 (3H, s), 2.40–1.90 (12H), 1.84 (3H, s), 1.62 (3H, s), 1.59 (3H, s), 1.35 (3H, s) |
|   |         | —CH₂OH | Oily 6.6 | 444 | 7.72 (2H, d, J = 8Hz), 7.30 (2H, d, J = 8Hz), 5.39 (1H, t, J = 6Hz), 5.18 (1H, t, J = 7Hz), 5.14–4.85 (2H, m), 3.99 (2H, s), 3.78 (2H, d, J = 8Hz), 2.44 (3H, s), 2.35–1.72 (13H), 1.67 (3H, s), 1.60 (6H, s), 1.35 (3H, s) |
| 3 | p-Tolyl | —COOH | Waxy 11.3 | 526 | 9.7 (1H, br), 7.75 (2H, d, J = 8Hz), 7.30 (2H, d, J = 8Hz), 6.88 (1H, t, J = 7Hz), 5.18 (1H, t, J = 7Hz), 5.10 (3H, br), 3.80 (2H, d, J = 8Hz), 2.44 (3H, s), 2.40–1.90 (16H), 1.84 (3H, s), 1.62 (3H, s), 1.60 (6H, s), 1.35 (3H, s) |
|   |         | —CH₂OH | Oily 10.5 | 512 | 7.72 (2H, d, J = 8Hz), 7.30 (2H, d, J = 8Hz), 5.39 (1H, t, J = 6Hz), 5.18 (1H, t, J = 7Hz), 5.14–4.85 (3H, m), 3.99 (2H, s), 3.80 (2H, d, J = 8Hz), 2.44 (3H, s), 2.35–1.72 (17H), 1.67 (3H, s), 1.60 (9H, s), 1.35 (3H, s) |
| 4 | p-Tolyl | —COOH | Waxy 2.1 | 594 | 9.7 (1H, br), 7.75 (2H, d, J = 8Hz), 7.30 (2H, d, J = 8Hz), 6.88 (1H, t, J = 7Hz), 5.18 (1H, t, J = 7Hz), 5.10 (4H, br), 3.80 (2H, d, J = 8Hz), 2.44 (3H, s), 2.40–1.90 (20H), 1.84 (3H, s), 1.62 (3H, s), 1.59 (9H, s), 1.35 (3H, s) |
|   |         | —CH₂OH | Oily 1.7 | 580 | 7.72 (2H, d, J = 8Hz), 7.30 (2H, d, J = 8Hz), 5.39 (1H, t, J = 6Hz), 5.18 (1H, t, J = 7Hz), 5.14–4.85 (4H, m), 3.99 (2H, s), 3.80 (2H, d, J = 8Hz), 2.44 (3H, s), 2.35–1.72 (21H), 1.67 (3H, s), 1.60 (12H, s), 1.35 (3H, s) |

The embodiments of the invention in which an exclusive property or privilege is claimed are defined as follows:

1. A process for producing a polyprenyl sulfone derivative of the formula:

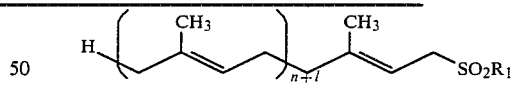

in a culture medium containing the compound of formula (II) until the compound of formula (I) is formed and then recovering the compound of formula (I) from the culture medium.

* * * * *

UNITED STATES PATENT AND TRADEMARK OFFICE
CERTIFICATE OF CORRECTION

PATENT NO. : 4 613 571
DATED : September 23, 1986
INVENTOR(S) : Akio Sato et al

It is certified that error appears in the above-identified patent and that said Letters Patent is hereby corrected as shown below:

On the title page, at item [73] change "Esai Co., Ltd." to ---Eisai Co., Ltd.---.

Signed and Sealed this

Seventh Day of April, 1987

Attest:

DONALD J. QUIGG

*Attesting Officer*  *Commissioner of Patents and Trademarks*